United States Patent [19]

Story et al.

[11] Patent Number: 5,730,598
[45] Date of Patent: Mar. 24, 1998

[54] PROSTHETIC IMPLANTS COATED WITH HYDROXYLAPATITE AND PROCESS FOR TREATING PROSTHETIC IMPLANTS PLASMA-SPRAYED WITH HYDROXYLAPATITE

[75] Inventors: Brooks Story, Carlsbad; Ann Burgess, San Clemente, both of Calif.

[73] Assignee: Sulzer Calcitek Inc., Carlsbad, Calif.

[21] Appl. No.: 814,735

[22] Filed: Mar. 7, 1997

[51] Int. Cl.⁶ .................................................. A61C 8/00
[52] U.S. Cl. ........................ 433/201.1; 433/173; 427/2.27
[58] Field of Search .............................. 433/173, 174, 433/201.1; 427/2.27

[56] References Cited

U.S. PATENT DOCUMENTS

| | | | |
|---|---|---|---|
| 4,146,936 | 4/1979 | Aoyagi et al. | 623/18 |
| 4,223,412 | 9/1980 | Aoyagi et al. | 433/201.1 |
| 4,366,183 | 12/1982 | Ghommidh et al. | 427/2.27 |
| 4,687,675 | 8/1987 | Nakano et al. | 427/2.27 |
| 4,693,986 | 9/1987 | Vit et al. | 501/1 |
| 4,702,930 | 10/1987 | Heide et al. | 427/2.27 |
| 4,746,532 | 5/1988 | Suzuki et al. | 427/2.27 |
| 4,839,215 | 6/1989 | Starling et al. | 428/131 |
| 4,861,733 | 8/1989 | White | 501/1 |
| 4,871,578 | 10/1989 | Adam et al. | 427/2.27 |
| 4,882,196 | 11/1989 | Shimamune et al. | 427/2.27 |
| 4,911,953 | 3/1990 | Hosonuma et al. | 427/2.27 |
| 4,919,751 | 4/1990 | Sumita et al. | 156/646 |
| 4,938,938 | 7/1990 | Ewers et al. | 423/308 |
| 4,960,646 | 10/1990 | Shimamune et al. | 428/471 |
| 4,963,145 | 10/1990 | Takagi et al. | 606/76 |
| 5,032,552 | 7/1991 | Nonami et al. | 501/95 |
| 5,034,352 | 7/1991 | Vit et al. | 501/1 |
| 5,039,546 | 8/1991 | Chung et al. | 427/2.27 |
| 5,108,399 | 4/1992 | Eitenmuller et al. | 606/77 |
| 5,141,576 | 8/1992 | Shimamune et al. | 148/254 |
| 5,180,564 | 1/1993 | Wahl et al. | 423/309 |
| 5,242,706 | 9/1993 | Cotell et al. | 427/2.27 |
| 5,306,305 | 4/1994 | Lee | 623/16 |
| 5,310,464 | 5/1994 | Redepenning | 204/180.2 |
| 5,405,436 | 4/1995 | Maurer et al. | 106/35 |
| 5,427,754 | 6/1995 | Nagata et al. | 423/308 |
| 5,441,536 | 8/1995 | Aoki et al. | 427/2.27 |
| 5,472,734 | 12/1995 | Perrotta et al. | 427/2.27 |
| 5,478,237 | 12/1995 | Ishizawa | 433/201.1 |
| 5,496,399 | 3/1996 | Ison et al. | 106/35 |
| 5,543,019 | 8/1996 | Lee et al. | 204/192.15 |

OTHER PUBLICATIONS

K. de Groot, *Plasma Sprayed Coatings Hydroxylapatite*, 1987, Journal of Biomedical Materials Research, vol. 21, 1375–1381.

H.W. Denissen et al, *Fluorapatite And Hydroxyapatite Heat–Treated Coatings For Dental Implants*.

K. de Groot, et al; *Plasma–Sprayed Coatings of Calcium Phosphate*; CRC Handbook of Bioactive Ceramics, vol. II, pp. 133–142.

Higashikata, Masaaki et al; *Characterization of Hydroxyapatite Coating Obtained by Hydrothermal Transformation of Plasma–Sprayed α–Tricalcium Phosphate*; Proceedings of the First International Symposium of Apatite, Mishima, Japan, Jul. 1991.

(List continued on next page.)

*Primary Examiner*—John J. Wilson
*Attorney, Agent, or Firm*—Philip S. Lyren

[57] ABSTRACT

An implant and a process for treating the same wherein the implant has a highly pure coating of crystalline hydroxylapatite (HA). The implant is initially coated with HA using a plasma spraying technique and is then subjected to a two stage process, including a hydrothermal treatment stage and a leaching stage. The resulting implant is highly crystalline, containing only a small percentage of amorphous calcium phosphate and essentially being free of calcium hydroxide, calcium oxide, and calcium carbonate.

23 Claims, 4 Drawing Sheets

OTHER PUBLICATIONS

S.R. Radin, P. Ducheyne; *Plasma spraying induced changes of calcium phosphate ceramic characteristics and the effect on in vitro stability*; Journal of Materials Science: Materials in Medicine 3 (1992) 33–42.

Z. Zyman; *Amorphous phase and morphological structure of hydroxyapatite plasma coatings*; Biomaterials 1993 vol. 14. No. 3.

Z. Zyman et al; *Periodic crystallization effect in the surface layers of coatings during plasma spraying of hydroxyapatite*; Biomaterials 1993, vol. 14, No. 15.

Masahiro Yoshimura et al; *Hydrothermal Processing of Hydroxyapatite: Past, Present, and Future*; 1994 by CRC Press, Inc.

Jie Weng, et al; *Intrinsic factors of apatite influencing its amorphization during plasma-spray coating*; Biomaterials 1995, vol. 16 No. 1.

Yang Cao et al; *Water vapour–treated hydroxyapatite coatings after plasma spraying and their characteristics*; Biomaterials 1996, vol. 17.

Harini Dasarathy et al; *Analysis of apatite deposits on substrates*; Journal of Biomedical Materials Research, vol. 27, 477–82 (1993).

J.G.C. Wolke et al; *Bioceramics For Maxillofacial Applications*.

Jie Weng et al; *Thermal decomposition of hydroxyapatite structure induced by titanium and its dioxide*; 1994 Chapman & Hall.

R.M. Pilliar et al; *Mechanical Characteristics of Plasma–Sprayed Hydroxyapatite–Titanium Alloy Interfaces*; Bioceramics vol. 4 (Proceedings of the 4th International Symposium on Ceramics in Medicine, London, UK, Sep. 1991).

Takeo Hattori et al; *Hydrothermal Synthesis of Hydroxyapatite from Calcium Acetate and Triethyl Phosphate*; Advanced Ceramic Materials 3 [4] 426–28 (1988).

D.M. Roy et al; *Hydrothermal Synthesis of Various Carbonate Containing Calcium Hydroxyapatites*; Mat.Res. Bull, vol. 9 pp. 35–40 ('74).

Jiyong Chen et al; *Effect of atmosphere on phase transformation in plasma–sprayed hydroxyapatite coatings during heat treatment*; Journal of Biomedical Materials Research, vol. 34, 15–20 (1997).

PROSTHETIC IMPLANTS COATED WITH HYDROXYLAPATITE AND PROCESS FOR TREATING PROSTHETIC IMPLANTS PLASMA-SPRAYED WITH HYDROXYLAPATITE

FIELD OF THE INVENTION

The present invention relates generally to implantable prosthetic implants for osseointegration and processes for treating the same, and more particularly to implants having a hydroxylapatite coating to promote osseointegration, and to processes for treating these implants plasma-sprayed with hydroxylapatite.

BACKGROUND OF THE INVENTION

Since the 1980's, a surge of technology has been directed toward producing dental implants that are extremely biocompatible with human tissue and bone. One goal of this technology is to produce an implant that as closely as possible resembles natural bone tissue. Such an implant would more fully integrate with existing bone tissue and enhance new bone growth around the implant.

Biological apatite is one of the major compounds occurring in human bones and teeth. A synthetic form of this mineral hydroxylapatite (HA) is very similar to the natural occurring apatite. This similarity between synthetic HA and naturally occurring apatite has lead scientists to pursue the use of HA with dental and orthopedic implants. One goal of this research is to produce an implant that readily integrates with surrounding bone and tissue after being implanted.

Some of the first dental implants attempting to employ synthetic apatite were completely formed from sintered HA. These implants had excellent bioactive properties once implanted. Scientists, however, learned that the mechanical properties of these implants were often insufficient. For example, dental implants formed solely from HA could not withstand normal physiological loading and were prone to crack and break after being implanted within human patients.

Investigation thereafter focused on using a metallic implant, such as those formed from a titanium substrate. Metallic implants are strong and able to withstand the physiological loading encountered within the jaw bone. These implants, however, do not osseointegrate as quickly as implants formed solely from HA. Attention was then directed toward coating metallic implants with HA.

Plasma spraying is one process known for coating metallic implants with HA. During this process, a stream of mixed gases passes through a high temperature electric arc that ionizes the gases into a plasma flame. Thereafter, crystalline HA feedstock powder is fed into the stream and then impinged in a molten state onto the outer surface of the implant. The spray adheres to the surface and forms a relatively thin coating of HA.

HA coated metallic implants exhibit the advantages of both purely metallic implants and purely HA implants. As such, these implants are strong, and bone tissue tends to form a strong bond with the surface of the coating and thus promote biocompatibility and osseointegration. Unfortunately, plasma spraying results in several important disadvantages.

Plasma spraying exposes HA to extremely high temperatures which, in turn, induce unwanted changes in morphology and chemical composition. These changes pose particular problems. In particular, it is known that highly crystalline HA has an in vitro stability that is much higher than non-crystalline HA. HA feedstock of a good quality does have a completely crystalline form before it is sprayed. The temperatures associated with plasma spraying, though, cause the HA to partially transform from its pure and crystalline form to one having a much less crystalline structure. This non-crystalline form of HA is commonly referred to as amorphous calcium phosphate (ACP). During plasma spraying, crystalline HA feedstock is also partially converted into other crystalline compounds, such as tricalcium phosphate (including $\alpha$-TCP and $\beta$-TCP), tetracalcium phosphate (TTCP), and calcium oxide (CaO). Collectively, these impurities may be referred to as crystalline soluble phases because their solubility in aqueous solutions is substantially higher than that of crystalline HA.

The impurities resulting from plasma spraying HA pose several problems. First, the impurities tend to dissolve into surrounding tissue. Thus, the plasma sprayed coating on the implant disintegrates over time as part of the coating is lost. It has been proposed that if the HA coating dissolves, the bioactive interface between the bone and the implant becomes less effective. The dissolution may in fact weaken the interface between the implant and surrounding bone, and more particularly the interface between the coating and the implant. Additionally, some of these impurities have a hemolytic effect in vitro. Notably, CaO has been shown to cause hemolysis. Much attention, therefore, has been directed toward converting the impurities present on the coating back into crystalline HA.

Heat treatment is one method used to restore the highly crystalline content of HA plasma-sprayed coatings. During this method, the coated implant is heated in air to a relatively high temperature, typically at least about 500 to 600 degrees Celsius. The high temperature recrystallizes some of the amorphous HA and simultaneously converts some of the soluble phases to crystalline HA. At the same time, the high temperature degrades the fatigue strength of the titanium alloy substrates. As such, heat treatment is not an acceptable method since implants need to maintain their strength and structural integrity.

Hydrothermal treatment is another method used to produce highly crystalline HA. One advantage of this method is that the temperature during treatment is generally lower than the temperature required for the heat treatment method. As a result, degradation of the metallic substrate does not occur.

Some hydrothermal treatments are carried out in an autoclave. HA coated implants, for example, are placed in the autoclave in the presence of water or an aqueous solution. The temperature and pressure of the autoclave are then increased. As the temperature rises, the water turns to steam which, in turn, elevates the pressure. The implants are sustained in this elevated temperature and pressure environment while the amorphous and soluble crystalline phases convert to crystalline HA.

One disadvantage associated with present hydrothermal treatments is the treated implant may still have a relatively high percentage of impurities, including amorphous and soluble crystalline phases. Some of the ACP, for example, does not recrystallize. Thus, an implant with an extremely high percentage of crystalline HA is not obtained. Dental implants with a high crystallinity are desirable for implantation.

Another disadvantage is that the overall treatment time of the hydrothermal process may be quite long. Some hydrothermal treatments, for example, require the implant to be exposed to an elevated temperature and pressure for many hours or even days. The ability to treat a large number of implants in a short time period is not possible with these methods.

As another disadvantage, present hydrothermally based methods do not affect all impurities present after plasma spraying. As a result, the treated implant has a higher amorphous and soluble crystalline phase content than is otherwise possible. Thus, a relatively high percentage of impurities remains even after the treatment is finished.

As a further disadvantage, some hydrothermal treatments require a relatively high temperature. This high temperature, as noted with the heat treatment method, degrades the strength of the metallic substrate.

As another disadvantage, some hydrothermal treatments require excessive operating conditions such as high pressures. An apparatus capable of providing an extremely high pressurized environment would be costly or impractical for producing a large number of treated implants.

As a further disadvantage, some hydrothermal treatments require the implant to be immersed in an aqueous solution for extended periods of time, exceeding many hours or even days. These treatments are designed to selectively dissolve non-HA components, leaving the desirable species intact. Immersing the implants in this manner may negatively effect the strength of the adhesive coating, weaken the tensile strength of the implant, or result in other unwanted side affects.

As yet another disadvantage, some hydrothermal treatments utilize a water-vapor environment in which the water contains carbon dioxide ($CO_2$). The carbon dioxide reacts with the HA coating on the implant to form calcium carbonate ($CaCO_3$).

SUMMARY OF THE INVENTION

The present invention relates to a dental implant, orthopedic prosthesis, or the like having a highly crystalline hydroxylapatite (HA) coating. The implant is initially coated with HA using a known plasma spraying technique. After being plasma sprayed with HA, the implant is subjected to a two stage process, including a hydrothermal treatment stage and a leaching stage. Together, these two stages produce an implant having a highly crystalline HA coating containing Only a small percentage of amorphous calcium phosphate (ACP). The coating also is essentially free of calcium hydroxide, calcium oxide, and calcium carbonate.

During the hydrothermal treatment stage, the implant is placed in a vessel or apparatus capable of attaining an elevated temperature and pressure environment. The implant is then heated under a pressurized condition while in the presence of a water vapor atmosphere. Once a desired temperature is reached, it may be sustained for a predetermined amount of time. The vessel or apparatus is vented, and the implant is allowed to cool. Thereafter, the implant is treated during the leaching stage. This stage includes exposing the implant to liquid water for a predetermined time period. The implant is then immediately exposed to an organic solvent, such as acetone, and is then allowed to air dry.

As one advantage, the treated implant has a coating with a high percentage of crystalline HA. As such, ACP and soluble crystalline phase impurities are completely or almost completely converted into crystalline HA or alternatively dissolved from the coating. The surface coating, for example, may be about 97% by weight crystalline HA.

As another advantage, the overall process time required to treat the implant after plasma spraying is relatively short.

The process time, which includes both the hydrothermal treatment stage and the leaching stage, may be as short as several hours. Thus, more implants may be cycled through the process during a given time period.

As another advantage, the present process treats for a large number of crystalline impurities. After plasma spraying, the coating often contains calcium oxide. During the hydrothermal treatment stage, this calcium oxide does not fully convert to crystalline HA. Instead, part of the calcium oxide converts to calcium hydroxide. Calcium hydroxide dissolves during the leaching stage. The treated implant thus includes neither calcium oxide nor calcium hydroxide.

As a further advantage, the hydrothermal treatment stage of the present invention does not require a relatively high temperature. As such, the strength of the metallic substrate is not degraded.

As another advantage, the hydrothermal treatment stage does not require an excessive pressure in order to yield an implant with a highly crystalline HA coating. Under certain operating scenarios, for example, the pressure may vary from about 250 psi to about 1100 psi to achieve a surface coating of at least 90% by weight crystalline HA. As such, an apparatus capable of withstanding impractical pressures is not required.

As a further advantage, the leaching stage may be performed in about two hours. Thus, the implants are not immersed in water or an aqueous solution for relatively long periods of time that may negatively effect the strength of the coating's adhesion, weaken the tensile strength of the implant, or result in other unwanted side effects.

As a further advantage, dissolved carbon dioxide is removed from the water before the implant is treated in the water-vapor environment during the hydrothermal treatment stage. As such, carbon dioxide does not react with the HA coating to form calcium carbonate.

The invention, accordingly, comprises the apparatus and method possessing the construction, combination of elements, and arrangement of parts that are exemplified in the following detailed description. For a fuller understanding of the nature and objects of the invention, reference should be made to the following detailed description taken in connection with the accompanying drawings.

DETAILED DESCRIPTION

Figure 1:
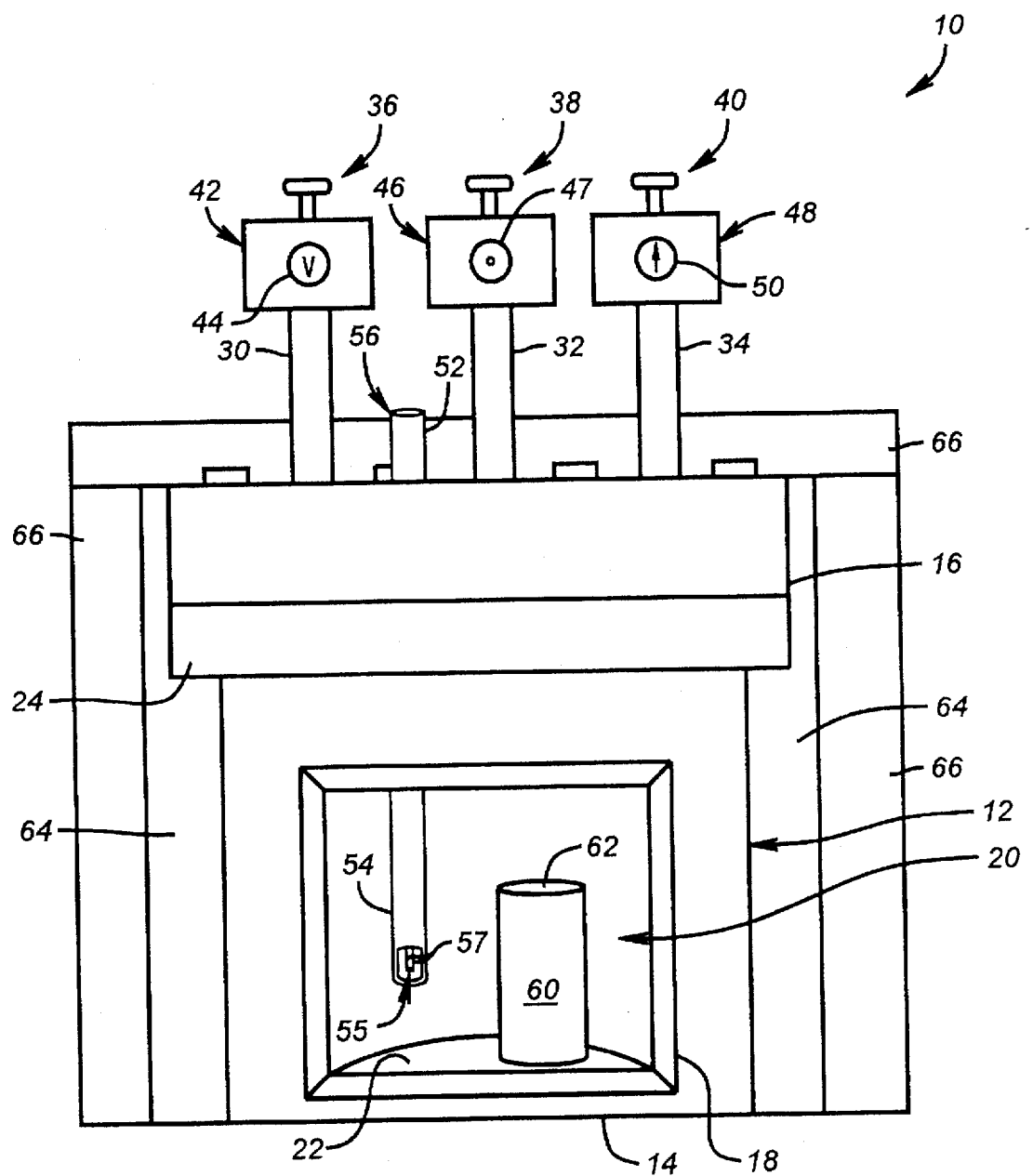
FIG. 1 is a schematic view partially cut away of a first embodiment of a reactor for carrying out the process of the present invention.

FIG. 1 illustrates a reactor 10 for carrying out the process of the present invention. Reactor 10 may be any one of various apparatus known to those skilled in the art capable of producing an elevated pressure and temperature environment, such as an autoclave or pressurizable vessel or chamber. Reactor 10 comprises a thick-walled, generally cylindrical pressurizable vessel 12 that includes a base portion 14 and a cover 16. Base portion 14 includes a cylindrical side wall 18 defining a cylindrical cavity 20 therein. Cavity 20 is open at the top end of base portion 14 and is closed at the bottom end. A planar bottom wall 22 integrally connects to side wall 18 to form the bottom enclosure. An annular flange 24 integrally connects to and extends radially outwardly from side wall 18 to form a top portion of base portion 14. The walls of vessel 12 are constructed with a material of sufficient strength and biocompatibility to provide a cavity 20 for sustaining an elevated temperature and pressure environment. These walls, for example, may be constructed of 316 stainless steel and provide cavity 20 with a volume of about 276 cubic centimeters.

Cover 16 is a generally planar disk constructed to fit tightly against annular flange 24. A heat-resistant gasket (not shown), such as a graphite gasket, is disposed between cover 16 and flange 24 to form a pressure-tight seal. A plurality of circumferentially spaced holes (not shown) extend through cover 16 and into flange 24. A plurality of corresponding threaded bolts 26 are disposable through these spaced holes. As bolts 26 are tightened, they bear against cover 16 and compress the gasket between the cover and flange 24 to effect a pressure-tight seal for cavity 20.

A plurality of conduits 30, 32, and 34 pass through cover 16. These conduits are sealed to the cover and communicate with cavity 20 to provide a pathway for ingress and egress of gas or other fluid. Each conduit 30, 32, and 34 is conveniently provided with a corresponding valve 36, 38, and 40, respectively, for stopping or controlling gas or fluid flow. An outer end 42 of conduit 30 includes a vent 44, and an outer end 46 of conduit 32 includes an inlet 47 that attaches to a source (not shown) of ultra high purity inert gas, such as helium or argon. This gas flows through conduit 32 and into cavity 20 and thereafter may be vented from the cavity through conduit 30. An outer end 48 of conduit 34 includes a gauge 50 that measures the gas pressure within cavity 20.

A thermal well 52 passes through and is sealed to cover 16. This well comprises a conduit that has one end 54 extending within cavity 20 and a second end 56 extending to the exterior of pressure vessel 12. Well 52 is closed at end 54 to preclude gas or fluid communication through the conduit to the exterior of vessel 12. As shown, end 54 extends into cavity 20 to be in thermal communication with the interior space of the cavity. A sufficient space exists between end 54 and the interior sidewalls of cavity 20 in order to maintain appropriate isolation for recording thermal measurements.

An electric thermocouple 55 is disposed within end 54 and exposed to the ambient temperature inside cavity 20. The thermocouple generates an electrical voltage that is proportionally related to the temperature inside the cavity. The thermocouple comprises two wires 57 that form a junction and extend the length of well 52 and connect to a proportional integral differential (PID) controller (not shown). The controller converts the generated electrical voltage to a convenient temperature scale for display and controls the operation of a heat source for reactor 10. A PID controller suitable for such use is model 942, manufactured by Watlow in Winona, Minn.

A removable reservoir 60 also is disposed within cavity 20. The reservoir comprises a cylindrical container having an open top 62. Liquid water of high purity is placed within reservoir 60 and exposed to the interior space of cavity 20.

An electric heating mantle 64 surrounds the exterior of the vessel and is used to heat the interior of cavity 20. During heating, thermocouple 55 senses the temperature of the interior of the cavity, and this information is sent to the PID controller. As the temperature of the cavity approaches a desired value, the controller reduces or terminates the rate at which heating mantle 64 delivers heat in order to prevent overshoot of the desired temperature.

A ceramic insulation blanket 66 surrounds vessel 12 and heating mantle 64. Preferably, the blanket has a thickness of at least about one inch and has a density of about eight pounds per cubic foot, which is sufficient to insulate the vessel.

Figure 2:
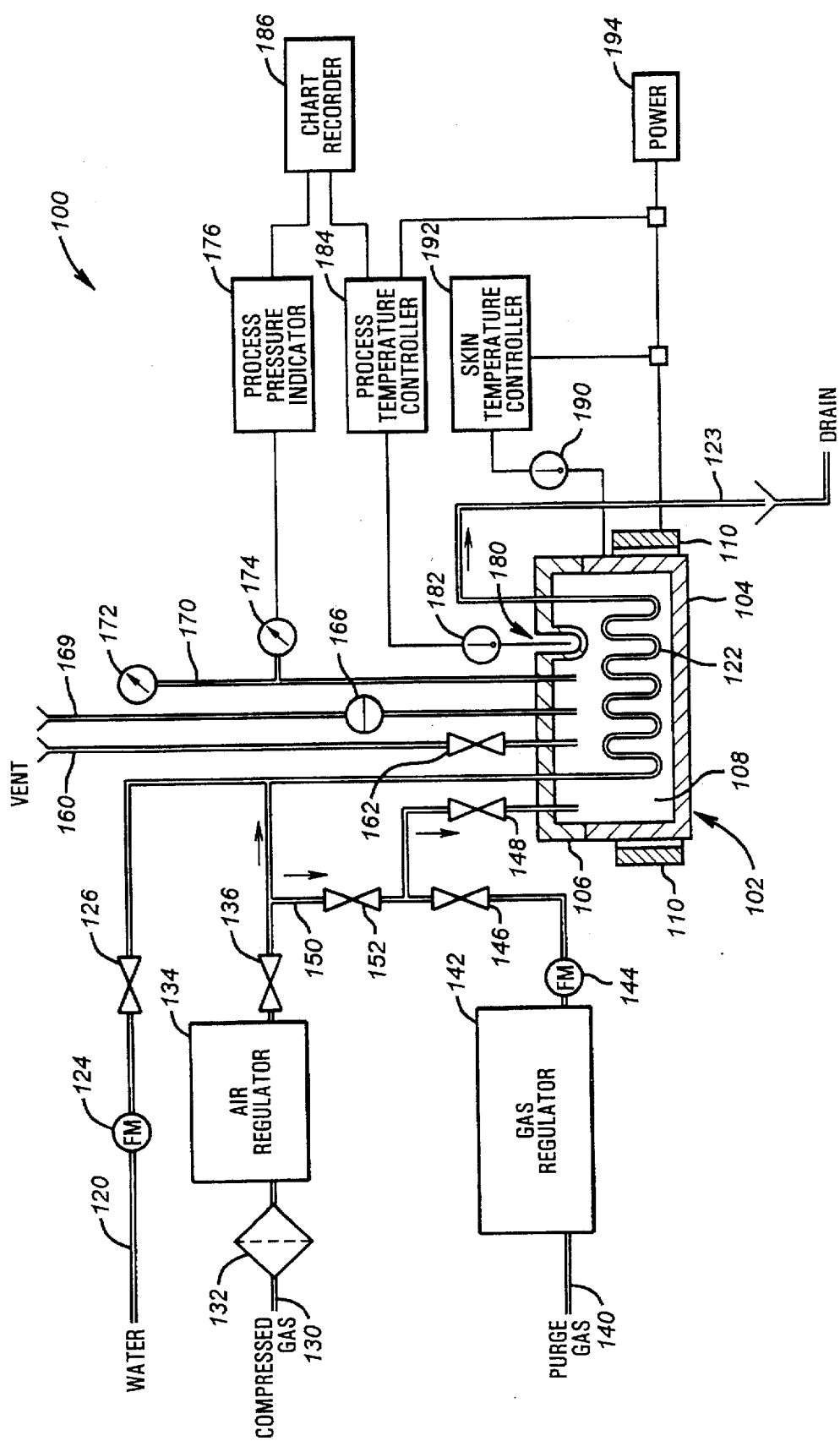
FIG. 2 is a schematic view of a second embodiment of a reactor for carrying out the process of the present invention.

FIG. 2 illustrates another reactor 100 for carrying out the process of the present invention and shows in more detail the system required to regulate the control of the reactor operations.

Reactor 100 generally includes a thick walled, pressurizable vessel 102 that includes a base portion 104 and a cover 106. Base portion 104 and cover 106 define a cavity 108. This cavity may be accessed when cover 106 is removed from base portion 104. A heater 110 heats cavity 108 to a desired temperature during operation.

Cover 106 is constructed to fit tightly against base portion 104. A heat resistant gasket (not shown) is disposed between cover 106 and base portion 104 to form a pressure tight seal. A plurality of bolts (not shown) past through the cover and base portion to effect this pressure tight seal for cavity 108.

A plurality of conduits and lines form part of reactor 100. These conduits and lines regulate and maintain the operation of the reactor and are more fully discussed below.

A water line 120 extends through cover 106 to a plurality of cooling coils 122. These coils extend within cavity 108 and connect to an external drain line 123 that provides an outlet for the cooling coils. Line 120 includes a flow meter 124 and a valve 126. Flow meter 124 measures water flow through line 120. The flow of water is adjustable from valve 126.

Next, a compressed air line 130 connects to water line 120 and also is in communication with cooling coils 122. Line 130 includes a compressor 132, an air regulator 134, and a valve 136. Compressor 132 compresses incoming filtered air. This compressed filtered air then passes through regulator 134 which regulates and controls the flow of air. The flow of this air is adjustable from valve 136.

An argon gas line 140 extends through cover 106 and is in communication with cavity 108. A gas regulator 142 regulates the flow of gas into line 140. After the regulator, the gas passes to a flow meter 144, which measures and controls the flow rate, and then passes through two valves 146 and 148. These two valves adjust the gas flow through line 140. Additionally, an artery 150 extends from air line 130 and connects to gas line 140. This artery includes a valve 152.

The system of valves communicating with the air and gas lines controls the flow of gas into cavity 108. If valves 152 and 148 are open and valve 146 is closed, then compressed air may flow into cavity 108 while gas is prohibited from flowing therein. If valves 146 and 148 are open and valve 152 is closed, then gas may flow into cavity 108 while air is prohibited from flowing therein.

During operation of reactor 100, the pressure, temperature, and steam content within cavity 108 should be closely monitored and regulated. A vent line 160 extends through cover 106 and includes a valve 162. When valve 162 is open, line 160 may be used to release steam or purge gas from cavity 108.

A safety line 164 also extends through cover 106 to communicate with cavity 108. Line 164 includes a rupture disk 166 that prevents an excess build up of pressure within cavity 108. If dangerous levels of pressure are experienced within the cavity, then disk 166 ruptures and vents this pressure through line 164.

As shown, a pressure line 170 extends through cover 106 to cavity 108 and includes two pressure transducers 172 and 174. Transducer 172 measures the pressure within cavity 108 and may be, for example, an analog type gauge. Transducer 174 also measures the pressure with cavity 108 and may be an electrical transducer device. Additionally, a process pressure indicator 176 is in communication with transducer 174 and provides a digital pressure readout.

A thermowell 180 extends into cavity 108. This well includes a thermocouple 182 and is connected to a process temperature controller 184. This controller displays a digital readout of the temperature inside cavity 108 and additionally is programmable to control the heating parameters, such as the heating time, hold time, and temperature. As shown, indicator 176 and controller 184 are connected to a chart recorder 186. This recorder records both pressure and temperature information and provides historical data.

Another thermocouple 190 also communicates with cavity 108. This thermocouple connects to a skin temperature controller 192 that prevents an excess temperature from occurring within cavity 108. Controllers 184 and 192 connect to a power source 194. This power source also powers heater 110.

Figure 3:
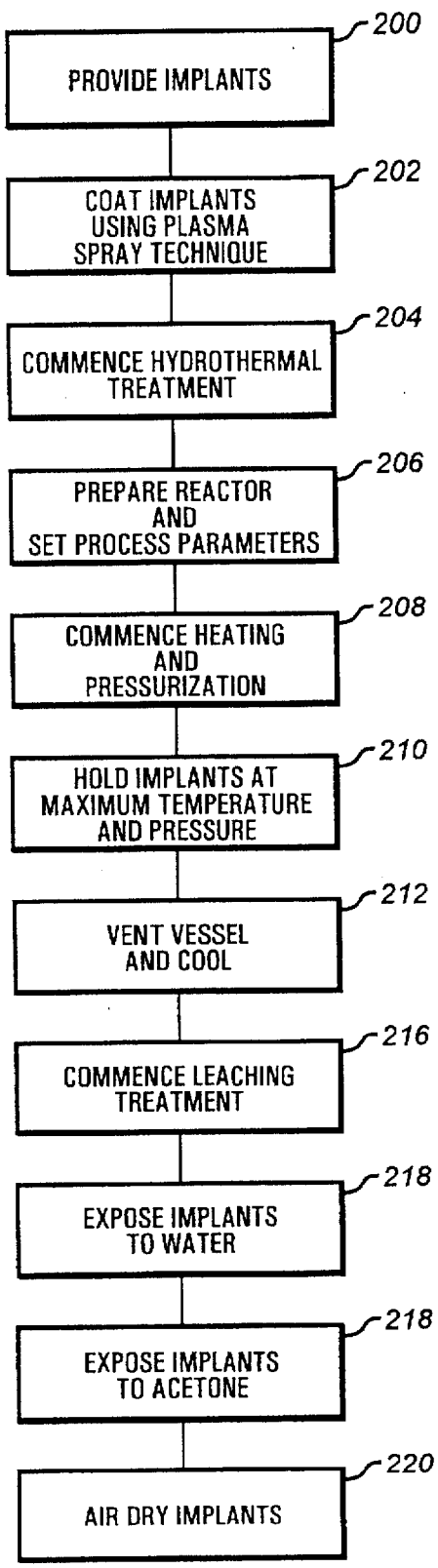
FIG. 3 is a flow chart summarizing the process of the present invention.

FIG. 3 shows an overview of the process of the present invention. The process generally includes a hydrothermal treatment stage followed by a leaching stage.

Per block 200, implants are provided. Next, as shown in block 202, the implants are coated with HA. Plasma spraying is used to coat the implants, and such coating techniques are widely known in the art. HA powder is used during the spraying process and preferably has a near 100% crystalline HA content. Once the implants are sprayed, they will have a coating comprising both crystalline HA and various impurities including ACP and soluble crystalline phases. The percentage of impurities may vary depending on numerous factors, such as the crystallinity of HA used and parameters during plasma spraying.

Once the implants are sprayed, they are ready for the hydrothermal treatment stage of the process, as shown in block 204. This stage is more fully illustrated in blocks 206 through 212.

Per block 206, the reactor is prepared. At this time, the implants are sealed in the vessel and the desired process parameters are established and set. Some of the process parameters include, for example, replacing the air in the vessel with an inert gas such as helium or argon and establishing the amount of water in the vessel, the rates at which the implants are heated and cooled, the maximum pressure and temperature, and the hold time for a given pressure and temperature.

Additionally, any dissolved carbon dioxide ($CO_2$) should be removed from the water in the vessel before heating commences. Carbon dioxide can react with the HA coating, specifically CaO or $Ca(OH)_2$, on the implant and form calcium carbonate ($CaCO_3$). Several methods exist for removing carbon dioxide from water, and these methods are known to those skilled in the art. Examples include boiling the water, bubbling gas (such as helium) through the water—a process known as gas sparging, or treating the water with a deionization apparatus.

As shown in block 208, the implants are then heated to the desired temperature. During this time, the pressure within the vessel increases and the water undergoes a phase change from liquid to saturated steam.

Next, as shown in block 210, the implants are held at maximum temperature and pressure for a given time period. For example, the implants may be held for 15 minutes at 300 degrees Celsius at a pressure of 1100 psi. Thereafter, steam is vented, and the vessel and implants are cooled, as shown in block 212.

After the hydrothermal treatment stage is completed, the implants should be at least about ninety percent (90%) by weight of crystalline HA. The calcium oxide present after plasma spraying is converted into calcium hydroxide.

As shown in block 214, the next step is to commence the leaching treatment. The leaching treatment removes the unwanted calcium hydroxide from the coating and leaves essentially a coating comprising crystalline HA and a small amount of ACP.

During the leaching treatment, the implants are exposed to water, as shown in block 216. Water dissolves the calcium hydroxide from the coating. One way to expose the implants to water is to immerse them in liquid water. Preferably, the water is agitated (for example stirred), and the implants remain in contact with the water for as long as two hours. The time period should be sufficient to dissolve as much of the calcium hydroxide as practical without subjecting the implants or coating to any unwanted side-effects.

After the implants are exposed to water, they are immediately exposed to dry acetone, as shown in block 218. The acetone acts to remove any residual water left on the implants. The implants may, for example, be submerged in an acetone bath for about 60 seconds. Submersion into successive acetone baths may be necessary to completely remove the excess water from the implants.

Finally, per block 220, the implants are allowed to air dry. During air drying, the acetone evaporates from the coating.

After the hydrothermal treatment and leaching treatment stages are complete, the implants should comprise a substrate having a coating that is highly crystalline HA. The coating should be about 90% to 100% by weight crystalline HA and essentially free of calcium oxide, calcium hydroxide, calcium carbonate, and soluble crystalline phases.

Looking back now to FIG. 1, a preferred mode of practicing the invention is given in more detail. Hydroxylapatite is plasma sprayed onto the exterior of the implant, such as a dental implant or an implantable prosthesis. Plasma spraying techniques are well known to those skilled in the art. After the implant has been HA coated, cover 16 is removed from flange 24, and the implant is placed within cavity 20 of vessel 12. A plurality of implants may be disposed within the cavity and placed on racks (not shown) to prevent direct contact with any interior wall or surface inside vessel 12. A select amount of high purity liquid water is then placed within reservoir 60. This water preferably should be treated to remove carbon dioxide by methods known to those skilled in the art, such as boiling, helium sparging, or de-ionization. The reservoir prevents the liquid water from directly contacting the implants. Cover 16 is placed on flange 24, and the bolts 26 are tightened to draw cover 16 tightly against flange 24 to effect a high quality pressure-tight seal. After vessel 12 is closed, valves 36 and 38, designated as the vent valve and gas supply valve, respectively, are opened. A source of ultra-pure inert gas, preferably helium or argon, flows through valve 38 and into cavity 20. As a result of this gas flow, the original atmosphere of air within cavity 20 is displaced through vent valve 36. The flow of gas is maintained for a period that is sufficient to purge cavity 20 of air and leave a completely inert atmosphere. Removal of air helps minimize oxidation of the titanium substrate which can result in discoloration of exposed metal surfaces. A purging period of about fifteen minutes with a gas flow rate of about 1770 cc/min. for production reactors has been found satisfactory.

After purging, the vent valve and gas supply valve are closed, sealing the inert gas atmosphere within cavity 20 at a pressure equal to about ambient atmospheric pressure. Heating mantle 64 is activated and heating of cavity 20 is commenced. During about the next sixty minutes, the interior temperature of cavity 20 rises from room temperature to a final temperature of about 300 degrees Celsius. The liquid water in reservoir 60 undergoes a phase change from liquid to gas, and generates a final pressure in the cavity of about 1100 pounds per square inch.

The temperature is held at about 300° Celsius for a period of about 15 minutes. After this time, valve 36 is opened, and the steam is vented to atmosphere, resulting in an immediate drop in pressure and temperature. Valve 36 is then closed to prevent entry of air as vessel 12 cools. Vessel 12 is removed from heating mantle 64 and allowed to cool until cover 16 can be safely removed without risk of warpage or injury to the vessel. Cooling to a temperature of about 100° Celsius over a period of about 45 minutes has been found satisfactory.

After cooling, vessel 12 is opened and the implant or rack of implants are removed from cavity 20. Subsequently, the implants and rack are immersed in distilled water at room temperature for about two hours. Preferably, the water is either stirred or the rack oscillated in order to produce a relative motion between the implants and water. The implants are then removed from the distilled water and are immediately submerged in a first bath of acetone for about 30 seconds. The rack and implants are withdrawn from the first bath of acetone and immediately submerged in a second bath of fresh acetone for about 30 seconds. The acetone baths essentially remove any liquid water from the implants and enable them to quickly air dry.

The process steps described above yield a hydroxylapatite coating comprising about 97% crystalline hydroxylapatite and being essentially free of calcium oxide, calcium hydroxide, soluble crystalline phases, and $CaCO_3$. The composition of the resultant coating was determined by X-ray diffraction analysis over a range of 20 from about 16° to about 40°. The metallic substrate showed no significant discoloration by oxidation. Additionally, no significant decrease in the strength of adhesion between the coating and the substrate existed.

Although a preferred mode of practicing the invention has been described above, it should be recognized that other process parameters and combinations can be employed within the scope of the invention. Such process parameters include, for example, the initial amount of water in the reservoir, the temperature in the cavity, the pressure in the cavity, the hold time for the pressure and temperature, and the length of time the implants undergo leaching. It is important to note, though, that one important advantage of the present invention is the process yields a hydroxylapatite coating being about 90% to 97% purity by weight. Further, the coating is virtually free of calcium oxide, calcium hydroxide, soluble crystalline phases, and $CaCO_3$. Thus, although the process parameters during both the hydrothermal and leaching stages may be varied, the resultant implants should have at least a 90% crystalline HA coating.

The examples below describe some of the possible various combinations of process parameters. In each of the following examples, the reactor described in FIG. 1 was employed. The treated implants in the following examples comprise titanium alloy strips (Ti6Al4V) coated with hydroxylapatite powder applied via a plasma spray process. Although the feedstock of the plasma spray operation was substantially 100% crystalline hydroxylapatite, the coating immediately after spraying comprised crystalline hydroxylapatite and impurities consisting of amorphous phases (ACP) and soluble crystalline phases, such as tri-calcium phosphate (including $\alpha$-TCP and $\beta$-TCP), tetracalcium phosphate (TTCP), and calcium oxide (CaO). The composition of the plasma sprayed coatings before any further treatment steps included the following components in the approximate ranges indicated: 28% to 46% crystalline hydroxylapatite, 40% to 52% non-crystalline hydroxylapatite (ACP), and 12% to 19% crystalline soluble components, including $\alpha$-TCP, $\beta$-TCP, TTCP, and CaO. CaO was present between about 0.4% to 2.0%. The HA crystallinity of all these coatings represents lower-end crystallinity than typically found in most commercially available implants. The coating thickness for these samples was 0.004–0.005" which is about twice as thick as commercially available implants. The x-ray diffraction method yielding the composition of the coating has been reported by LeGeros, John P., et al, "ASTM STP 1196."

EXAMPLE 1

Titanium alloy implants were plasma-sprayed with HA and then placed in reactor 10. The reactor was then charged with 20.4 grams of water, closed, and purged with ultra-pure helium for 15 minutes at a rate of 400 cc/min. Heating was initiated. After 59 minutes, the interior of cavity 20 reached a temperature of 282° C. and a pressure of 925 psi. Reactor 10 was then vented to atmospheric pressure and removed from heating mantle 50. X-ray diffraction analysis of the treated implants showed that the coating contained 94.5% crystalline hydroxylapatite, 4.7% amorphous calcium phosphate, and 0.8% $Ca(OH)_2$. No traces of TCP, TTCP or CaO were detected. A treated implant was subsequently stirred in distilled water for two hours at room temperature and twice dipped in fresh acetone for thirty seconds. X-ray diffraction analysis showed that the steam-treated implant contained 0.4% $Ca(OH)_2$.

EXAMPLE 2

Titanium alloy implants were plasma-sprayed with HA and then placed in reactor 10. The reactor was then charged with 10.0 grams of water, closed, and purged with ultra-pure helium for 15 minutes at a rate of 400 cc/min. Heating was initiated. After 40 minutes, the interior of cavity 20 reached a temperature of 300° C. and a pressure of 390 psi. The reactor 10 was then vented to atmospheric pressure and removed from heating mantle 50. X-ray diffraction analysis of the treated implants showed that the coating contained 70.6% crystalline hydroxylapatite, 25.8% amorphous calcium phosphate, 3.0% $Ca(OH)_2$ and 0.7% CaO. No traces of TCP or TTCP were detected. A treated implant was subsequently stirred in distilled water for two hours at room temperature and twice dipped in fresh acetone for thirty seconds. X-ray diffraction analysis showed that the steam-treated implant contained 1.2% $Ca(OH)_2$ and 0.5% CaO.

EXAMPLE 3

Titanium alloy implants were plasma-sprayed with HA and then placed in reactor 10. The reactor was then charged with 23 grams of water, closed, and purged with ultra-pure helium for 15 minutes at a rate of 400 cc/min. Heating was initiated. After 30 minutes, the interior of cavity 20 reached a temperature of 170° C. The temperature was maintained at 170° C. for 135 minutes, at which time the pressure was measured at 160 psi. The reactor 10 was then vented to atmospheric pressure and removed from heating mantle 50. X-ray diffraction analysis of the treated implants showed that the coating contained 88.0% crystalline hydroxylapatite, 10.8% amorphous calcium phosphate, and 1.1% $Ca(OH)_2$. No traces of TCP, TTCP or CaO were detected. A treated implant was subsequently stirred in distilled water for two hours at room temperature and twice dipped in fresh acetone for thirty seconds. X-ray diffraction analysis showed that the steam-treated implant contained 0.3% $Ca(OH)_2$.

EXAMPLE 4

Titanium alloy implants were plasma-sprayed with HA and then placed in reactor 10. The reactor was then charged with 12.3 grams of water, closed, and purged with ultra-pure helium for 15 minutes at a rate of 400 cc/min. Heating was initiated. After 44 minutes, the interior of cavity 20 reached a temperature of 206° C. The temperature was maintained at 206° C. for 45 minutes, at which time the pressure was measured at 250 psi. The reactor 10 was then vented to atmospheric pressure and removed from heating mantle 50. X-ray diffraction analysis of the treated implants showed that the coating contained 90.2% crystalline hydroxylapatite, 8.8% amorphous calcium phosphate, and 0.9% $Ca(OH)_2$. No traces of TCP, TTCP or CaO were detected. A treated implant was subsequently stirred in distilled water for two hours at room temperature and twice dipped in fresh acetone for thirty seconds. X-ray diffraction analysis showed that the steam-treated implant contained 0.6% $Ca(OH)_2$.

EXAMPLE 5

Titanium alloy implants were plasma-sprayed with HA and then placed in reactor 10. The reactor was then charged with 20 grams of water, closed, and purged with ultra-pure helium for 15 minutes at a rate of 400 cc/min. Heating was initiated. After 60 minutes, the interior of cavity 20 reached a temperature of 300° C. The temperature was maintained at 300° C. for 15 minutes, at which time the pressure was measured at 1100 psi. The reactor 10 was then vented to atmospheric pressure and removed from heating mantle 50. X-ray diffraction analysis of the treated implants showed that the coating contained 97.0% crystalline hydroxylapatite, 3.0% amorphous calcium phosphate, and 0.0% $Ca(OH)_2$. No traces of TCP, TTCP or CaO were detected. A treated implant was subsequently stirred in distilled water for two hours at room temperature and twice dipped in fresh acetone for thirty seconds. X-ray diffraction analysis showed that the steam-treated implant contained 0.0% $Ca(OH)_2$.

The process parameters of the above examples are summarized in the following table. These examples illustrate that certain combination of process parameters are required to produce HA coatings having the desired chemical composition and crystalline content.

| | Example | | | | |
|---|---|---|---|---|---|
| | 1 | 2 | 3 | 4 | 5 Preferred |
| Parameter | | | | | |
| Helium purge rate | 400 cc/min | 400 cc/min | 400 cc/min | 400 cc/min | 400 cc/min |
| Helium purge time | 15 min | 15 min | 15 min | 15 min | 15 min |
| Water charge | 20.4 g | 10.0 g | 23.0 g | 12.3 g | 20 g |
| Heat-up time | 59 min | 40 min | 30 min | 44 min | 60 min |
| Final temperature | 282° C. | 300° C. | 170° C. | 206° C. | 300° C. |
| Final pressure | 925 psi | 390 psi | 160 psi | 250 psi | 1100 psi |
| Hold time | 0 min | 0 min | 135 min | 45 min | 15 min |
| $H_2O$ leaching time | 2 hr | 2 hr | 2 hr | 2 hr | 2 hr |
| | Coating Composition (%) | | | | |
| Coating component | Post-Plasma Sprayed → Post-Heat/Steam Treated | | | | |
| Crystalline HA | 45.3 → 94.5 | 28.8 → 70.6 | 44.0 → 88.0 | 46.2 → 90.2 | X → 97.0 |
| ACP | 42.0 → 4.7 | 52.3 → 25.8 | 42.1 → 10.8 | 40.0 → 8.8 | X → 3.0 |
| TCP | 7.6 → 0.0 | 9.0 → 0.0 | 7.9 → 0.0 | 7.6 → 0.0 | X → 0.0 |
| TTCP | 4.7 → 0.0 | 8.0 → 0.0 | 5.3 → 0.0 | 5.7 → 0.0 | X → 0.0 |
| | Coating Composition (%) | | | | |
| Coating component | Post-Plasma Sprayed → Post-Heat/Steam/Leach Treated | | | | |
| CaO | 0.4 → 0.0 | 2.0 → 0.5 | 0.8 → 0.0 | 0.6 → 0.0 | X → 0.0 |
| $Ca(OH)_2$ | 0.0 → 0.4 | 0.0 → 1.2 | 0.0 → 0.3 | 0.0 → 0.6 | X → 0.0 |

A further example below describes a preferred combination of process parameters for the reactor described in FIG. 2. The implants employed in the following example have similar characteristics to those described in connection with FIG. 1.

EXAMPLE 6

Titanium alloy implants were plasma-sprayed with HA and then placed in reactor 100. The reactor was then charged with about 200 cc of water, closed, and purged with ultra-pure argon for 20 minutes at a rate of 17.7 lpm. The water boiling time was 15 minutes and heating was initiated. The interior of the cavity reached a temperature of about 300° C., and the dwell time was 10 minutes. Reactor 100 was then vented to atmospheric pressure and removed from the heating mantle. The treated implant was subsequently stirred in distilled water at an agitation rate of 50 rpm for two hours at room temperature and then twice dipped in fresh acetone for one minute and five minutes, respectively.

The process parameters for this example were run three separate times. The results for each run are shown below in the table:

| Coating Component | Initial To Final Composition (%) | | |
|---|---|---|---|
| | Run #1 | Run #2 | Run #3 |
| Crystalline HA | 76.8→95.3 | 79.7→96.1 | 74.4→97.6 |
| ACP | 13.7→4.7 | 12.0→3.9 | 17.8→2.0 |
| β-TCP | 2.1→0.0 | 1.9→0.0 | 2.1→0.0 |
| α-TCP | 0.7→0.0 | 0.3→0.0 | 0.5→0.0 |
| TTCP | 5.9→0.0 | 5.1→0.0 | 4.5→0.0 |
| CaO | 1.0→0.0 | 0.9→0.0 | 0.7→0.0 |
| Ca(OH)$_2$ | 0.0→0.0 | 0.0→0.0 | 0.0→0.3 |
| CaCO$_3$ | 0.0→0.0 | 0.0→0.0 | 0.0→0.0 |
| AVERAGES | CRYSTALLINE HA: | 77.0→96.3 | |
| | ACP: | 14.5→3.5 | |
| | SOLUBLE PHASE: | 8.6→0.1 | |

Run #3 yielded the preferred results and shows that the coating on the treated implant contained 97.6% crystalline hydroxylapatite, 2.0% amorphous calcium phosphate, and 0.3% Ca(OH)$_2$. No traces of TCP, TTCP, CaO, or CaCO$_3$ were detected.

The preceding examples illustrate a temperature range between approximately 170° C. and 300° C. It would be obvious to one skilled in the art to increase the temperature to achieve a high crystalline coating component.

Figure 4:
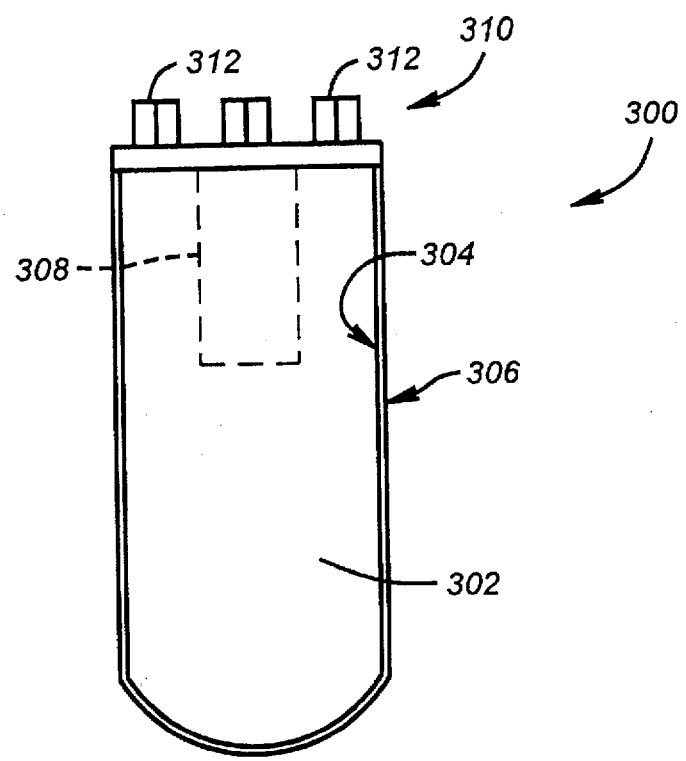
FIG. 4 is a cross-sectional view of a dental implant having an HA coating treated with the process of the present invention.

FIG. 4 illustrates an exemplary dental implant 300 treated with the process of the present invention. Dental implant 300 includes a substantially cylindrical, elongate substrate 302 composed of biocompatible titanium alloy. An outer surface 304 of substrate 302 is coated by an adherent layer 306 comprising substantially crystalline hydroxylapatite. Layer 306 is preferred to comprise at least about 90% by weight of crystalline hydroxylapatite, and is more preferred to comprise at least about 95% by weight of crystalline hydroxylapatite, and is most preferred to comprise at least about 97% by weight of crystalline hydroxylapatite. Layer 306 also is preferred to be essentially free of calcium oxide and to be essentially free of calcium hydroxide and calcium carbonate. As used herein, the term "essentially free of" means no more than about 1% by weight of crystalline soluble phases.

It should be noted that implant 300 represents one example of a dental implant. Other types of implants, dental implants and other implantable prosthesis known to those skilled in art, also may be treated with the process of the present invention. In this regard, the implant of FIG. 4 is shown to include a central coaxial threaded bore 308 open at one end 310. Extending upwardly from this end are a plurality of splines 312 used to interface with an auxiliary component (not shown), such as an abutment. This spline interface is fully taught in U.S. Pat. No. 5,449,291 entitled "Dental Implant Assembly Having Tactile Feedback."

Since certain changes may be made in the above-described apparatus and process without departing from the scope of the invention herein involved, all matter contained in the description or shown in the accompanying drawings shall be interpreted as illustrative and not in a limiting sense. We claim:

1. A method for producing an implant having a coating of at least about 90% by weight of crystalline hydroxylapatite, comprising the steps of: plasma spraying said implant with hydroxylapatite; placing said implant in a sealable, pressurizable vessel; heating said implant in the presence of steam while in said vessel; cooling said implant; and rinsing said implant with water.

2. The method of claim 1 further comprising the step of removing carbon dioxide (CO$_2$) from said steam before said step of heating said implant.

3. The method of claim 1 in which said heating step includes heating said implant to at least about 250 degrees Celsius at a final pressure of at least about 270 pounds per square inch.

4. The method of claim 1 further comprising the steps of: rinsing said implant in acetone to remove water after said rinsing step; and drying said implant in air to remove said acetone.

5. A method for treating a dental implant, comprising the steps of: plasma spraying said implant with a coating of hydroxylapatite, wherein said coating includes a crystalline phase of hydroxylapatite, amorphous calcium phosphate, calcium oxide, tri-calcium phosphates (including α-TCP and β-TCP), and tetracalcium phosphate; heating said implant while in a pressurized environment in the presence of water; converting said amorphous calcium phosphate to crystalline hydroxylapatite; converting said calcium oxide to calcium hydroxide; exposing said implant to an aqueous environment; and dissolving said calcium hydroxide from said coating.

6. The method of claim 5 further comprising the step of removing carbon dioxide (CO$_2$) from said water before said step of heating said implant.

7. The method of claim 5 in which said heating step includes heating said implant to a final temperature of between about 250 to 300 degrees Celsius at a final pressure of between about 800 to 1100 pounds per square inch, wherein said implant is maintained at said final temperature and said final pressure for about 0 to 20 minutes.

8. The method of claim 5 further comprising the steps of: converting said tri-calcium phosphates (including α-TCP and β-TCP) to crystalline hydroxylapatite; and converting said tetracalcium phosphate to crystalline hydroxylapatite.

9. The method of claim 5 in which said exposing step includes submersing said implant in water for between about one to two hours.

10. The method of claim 5 in which said heating step includes heating said implant until said coating has at most about 5% by weight of said amorphous calcium phosphate.

11. The method of claim 5 in which said heating step includes heating said implant until said coating has at most about 1% by weight of said calcium hydroxide.

12. A process for purifying a coating on an implant, comprising the steps of: plasma spraying said implant with hydroxylapatite to produce a first coating including both crystalline hydroxylapatite and non-crystalline hydroxylapatite; hydrothermally treating said first coating at a temperature above 200 degrees Celsius but below a temperature of about 300 degrees Celsius to convert said first coating into a second coating, wherein a portion of said non-crystalline hydroxylapatite of said first coating converts to crystalline hydroxylapatite to produce said second coating having a greater percent by weight of crystalline hydroxylapatite than said first coating; and leaching said second coating to convert said second coating into a final coating, wherein calcium hydroxide in said second coating is dissolved to produce said final coating having a greater percent by weight of crystalline hydroxylapatite than said second coating.

13. The process of claim 12 in which said steps of hydrothermally treating and leaching produce said final coating having about 97% by weight of crystalline hydroxylapatite.

14. The process of claim 12 in which: said step of hydrothermally treating further comprises the step of: heating said implant in a pressurized water-vapor environment, and cooling said implant; and said step of leaching further comprises the step of submersing said implant in water.

15. The process of claim 12 in which: said first portion of said non-crystalline hydroxylapatite includes tri-calcium phosphates (including α-TCP and β-TCP), tetra-calcium phosphate, and amorphous calcium phosphate; and said second portion of said non-crystalline hydroxylapatite includes tri-calcium phosphates, tetra-calcium phosphate, and amorphous calcium hydroxide.

16. A process for treating an implant for implantation in bone to achieve osseointegration, said process comprising the steps of: providing an implant; plasma-spraying hydroxylapatite on said implant to form a first preliminary coating on said implant; heating said implant and said first preliminary coating in a water-vapor atmosphere to convert said first preliminary coating to a second preliminary coating comprising at least about 90% by weight of crystalline hydroxylapatite; and exposing said implant and said second preliminary coating to liquid water to convert said second preliminary coating to a final coating comprising a greater percentage by weight of crystalline hydroxylapatite than said second preliminary coating.

17. The process of claim 16 in which said final coating comprises between about 90% to 98% by weight of crystalline hydroxylapatite.

18. A dental implant, comprising: a substrate; and a surface coating on said substrate, wherein said coating comprises plasma-sprayed hydroxylapatite having at least about 95 percent by weight of crystalline hydroxylapatite.

19. The dental implant of claim 18 in which said coating is essentially free of calcium oxide and calcium hydroxide.

20. The dental implant of claim 18 in which said surface coating is prepared by: plasma-spraying hydroxylapatite on said substrate to form a first preliminary coating on said substrate; heating said substrate and said first preliminary coating in a water-vapor atmosphere to convert said first preliminary coating to a second preliminary coating comprising at least about 90% by weight of crystalline hydroxylapatite; and exposing said substrate and said second preliminary coating to liquid water to convert said second preliminary coating to a final coating that is essentially free of calcium oxide, calcium hydroxide, and calcium carbonate.

21. An implant for implantation in bone to achieve osseointegration, comprising: a substrate; and a surface coating on said substrate comprising plasma-sprayed hydroxylapatite, wherein said surface coating, as determined by X-ray diffraction analysis over a range of 2θ from about 16° to about 40°, includes at least about 90 percent by weight of crystalline hydroxylapatite and is essentially free of calcium oxide and calcium hydroxide.

22. The implant of claim 21 in which said coating is treated with a two stage process including a hydrothermal treatment stage and then a leaching stage.

23. The implant of claim 21 in which said coating comprises about 97% by weight of crystalline hydroxylapatite after said substrate is heated in a water-vapor atmosphere to a final temperature of about 300° Celsius and a final pressure of about 1100 pounds per square inch and held at said final temperature and said final pressure for about 15 minutes.

* * * * *